US00PP35506P2

(12) United States Plant Patent
Robb

(10) Patent No.: US PP35,506 P2
(45) Date of Patent: Nov. 28, 2023

(54) ***MAGNOLIA* PLANT NAMED 'HYB01'**

(50) Latin Name: ***Magnolia laevifolia* x *figo***
Varietal Denomination: HYB01

(71) Applicant: Paradise Seed Company Limited, Kulnura (AU)

(72) Inventor: John B. Robb, Kariong (AU)

(73) Assignee: The Paradise Seed Company Limited, Kulnura (AU)

( * ) Notice: Subject to any disclaimer, the term of this patent is extended or adjusted under 35 U.S.C. 154(b) by 0 days.

(21) Appl. No.: 18/184,538

(22) Filed: Mar. 15, 2023

(51) Int. Cl.
*A01H 5/00* (2018.01)
*A01H 6/00* (2018.01)

(52) U.S. Cl.
USPC ..... Plt./223

(58) Field of Classification Search
USPC ..... Plt./223
See application file for complete search history.

*Primary Examiner* — Susan McCormick Ewoldt
(74) *Attorney, Agent, or Firm* — Weatherly IP Solutions, LLC; James M. Weatherly

(57) ABSTRACT

A new cultivar of *Magnolia* plant named 'HYB01' that is characterized by its compact well-branched plant habit, self-cleaning fragrant red-purple flowers borne in profusion in spring and a high tolerance of heat and humidity.

2 Drawing Sheets

Genus and species *Magnolia laevifolia* x *figo*.
Variety denomination: 'HYB01'.

BACKGROUND OF THE NEW PLANT

The present invention relates to a new and distinct cultivar of *Magnolia*, grown as an ornamental plant for use in the garden and landscape. The new cultivar is known botanically as *Magnolia laevifolia* x *figo* and will be referred to hereinafter by the cultivar name 'HYB01'. This application is co-pending with the application for the inventor's variety of *Magnolia* plant named 'SL01' (U.S. Plant patent application Ser. No. 18/185,368).

'HYB01' arose from a breeding program conducted by the inventor in Kariong, New South Wales, Australia. The breeding program was commenced in 2000 with the objectives of developing varieties of *Magnolia* which are suitable for pot or container production, with compact plant habits and profuse flowering in a range of flower colors.

The male parent of 'HYB01' is an unnamed *Magnolia laevifolia* (species, unpatented) and the female parent of 'HYB01' is an unnamed *Magnolia figo* (species unpatented). In 2000, the inventor first emasculated flowers of male *Magnolia laevifolia* and covered the emasculated flowers to exclude other pollination. The emasculated flowers were hand-pollinated by the inventor using pollen from *Magnolia figo*. The inventor collected the resultant seed from this controlled pollination and evaluated the growth and appearance of the hybrids until 2005 when the inventor selected 'HYB01'

The inventor first propagated 'HYB01' in 2005, using stem cuttings. The inventor has determined that 'HYB01' is stable and remains true to type in successive generations of asexual propagation.

SUMMARY

The following traits have been repeatedly observed and represent the characteristics of the new *Magnolia* cultivar 'HYB01'. 'HYB01' has not been tested under all possible conditions and phenotypic differences may be observed with variations in environmental, climatic and cultural conditions, however, without any variance in genotype.

1. 'HYB01' exhibits a compact and well-branched plant habit.
2. A seven year old plant of 'HYB01' growing in a large container, achieves a height of 125 cm. and a width of 100 cm.
3. 'HYB01' flowers profusely in spring, bearing approximately 500 flowers at peak flowering in mid to late March.
4. The ground color of the tepals of the flowers of 'HYB01' are pale cream-pink and heavily overlaid with light to dark red-purple mottling or flecks.
5. The tepals of the flowers exhibit darker red-purple tepal margins.
6. The flowers of 'HYB01' are self-cleaning and liable to shatter when touched.
7. The foliage of 'HYB01' is dark olive-green in color.
8. 'HYB01' grows well in moist well-drained soils in full sun to partial shade.
9. 'HYB01' exhibits a high tolerance of heat and humidity.
10. 'HYB01' is hardy at least to USDA Zone 6.

BRIEF DESCRIPTION OF THE PHOTOGRAPHS

The accompanying color photographs illustrate the overall appearance of the new *Magnolia* variety 'HYB01' showing colors as true as it is reasonably possible to obtain in colored reproductions of this type. Colors in the photographs may differ from the color values cited in the detailed botanical description, which accurately describe the actual colors of the new variety 'HYB01'. Photographs were taken in Santa Barbara, Calif. from a seven year old plant which is growing outdoors in a 15 gallon container. No chemicals were used to treat the plant.

BOTANICAL DESCRIPTION OF THE PLANT

Figure 1:
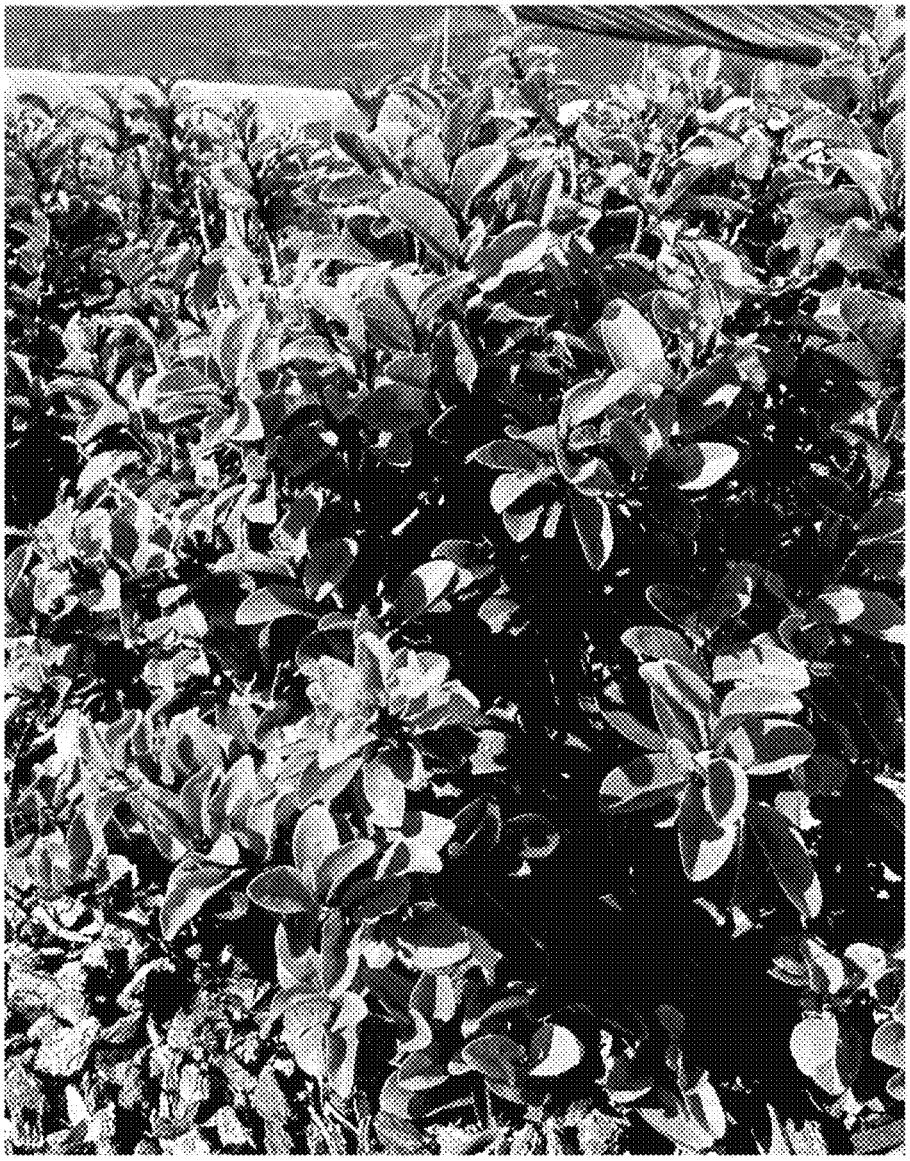
FIG. 1 depicts a whole plant of 'HYB01' in early bud.
Figure 2:
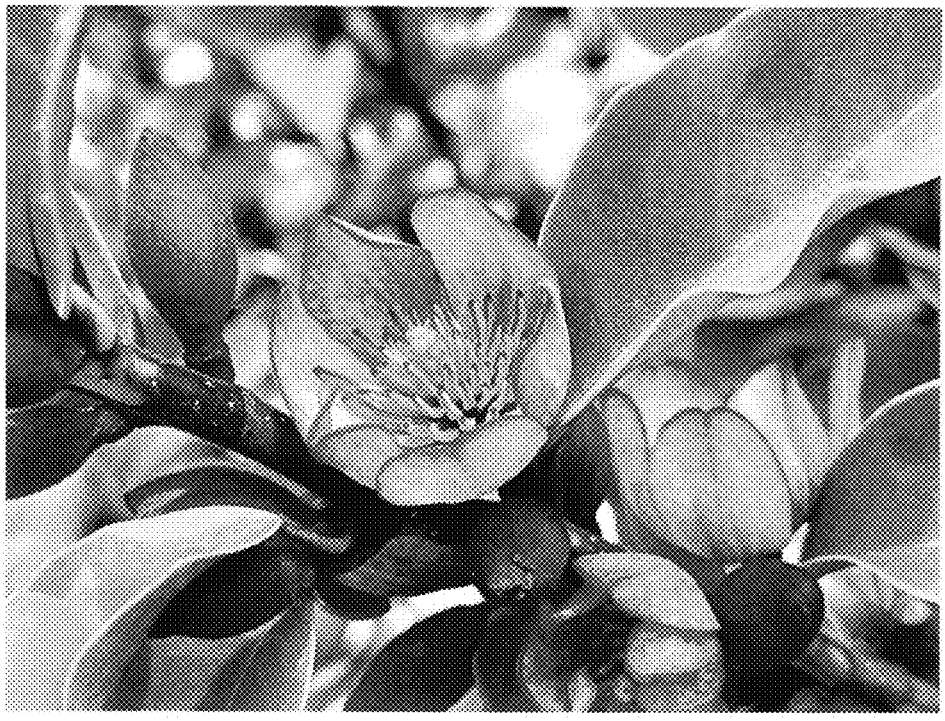
FIG. 2 depicts a close-up view of the buds and flowers of 'HYB01'.

The following is a detailed description of the new cultivar 'HYB01'. Data was collected from seven-year old plants grown in 15 gallon containers in Santa Barbara, Calif. The color determinations are in accordance with the 2007 edition of The Colour Chart of The Royal Horticultural Society, London, England, except where general color terms of ordinary dictionary significance are used. No chemicals were used to treat the plants. Growing conditions are typical of other *Magnolia*.

Botanical classification: *Magnolia*.

*Variety*.—'HYB01'.

*Species*.—*laevifolia* x *figo*.

Parentage:

*Male parent*.—Unnamed *Magnolia laevifolia*.

*Female parent*.—Unnamed *Magnolia figo*.

Plant description:

*Growth habit*.—Upright, broad vase-shaped.

*Use*.—In containers and for planting in the landscape.

*Suitable container sizes*.—3 gallon, 5 gallon and larger containers.

*Dimensions in seventh year (the observed plants) in a 5 gallon container*.—125 cm. in height, and 100 cm. in width.

*Hardiness*.—At least hardy to USDA Zone 6.

*Propagation*.—Stem cuttings.

*Root system*.—Fibrous.

*Light*.—Plant or position container in full sun or partial shade.

*Soil*.—Plant in moist but well drained soil.

*Type*.—Evergreen small tree.

*Seasonal interest*.—Red-purple flowers in early and mid-spring.

Stem (from soil level to first primary branch):

*Shape*.—Round cross-section.

*Dimensions*.—5 cm.-8 cm. in length, 5 cm. in diameter at soil level.

*Color*.—198D.

*Surface*.—Lignified, rough, glabrous. Lenticels absent.

Branches:

*Quantity*.—3 primary branches at or up to 8 cm. above soil level. 30-35 secondary branches or laterals.

*Branch dimensions*.—Primary branches: 70 cm.-90 cm. in length, 5 mm.-8 mm. in diameter. Secondary branches: 45 cm.-60 cm. in length.

*Branch shape*.—Geniculate (angled at each node), round cross-section.

*Internode distance*.—2.0 cm.-2.5 cm.

*Color*.—Older wood (2 or more years old): As stem, 198D. Newer growth (current and previous years): 151A-153D.

*Surface*.—Older wood (2 or more years old): Rough, longitudinally ridged. Newer growth (current and previous years): Smooth, with dense very dark brown pubescence. Hairs fine and very short (less than 0.25 mm.), color 200A.

Foliage:

*Leaf arrangement*.—Alternate.

*Leaf division*.—Simple.

*Leaf shape*.—Ovate, longitudinally convex.

*Leaf aspect*.—Ranges between 20 degrees to 40 degrees above the horizontal.

*Leaf attachment*.—Short petiolate.

*Petiole dimensions*.—6 mm.-9 mm. in length and 2 mm.-3 mm. in diameter.

*Petiole color*.—Ranges between 151A-153D.

*Leaf dimensions*.—70 mm.-80 mm. in length, 40 mm.-43 mm. in width.

*Leaf surface (adaxial)*.—Smooth, glabrous, glossy.

*Leaf surface (abaxial)*.—Smooth, glabrous, matte.

*Leaf color (adaxial)*.—146A.

*Leaf color (abaxial)*.—146D.

*Leaf apex*.—Rounded.

*Leaf base*.—Broadly acute, almost rounded.

*Leaf margin*.—Smooth, entire.

*Leaf venation pattern*.—Pinnate.

*Veins (adaxial surface)*.—Appear as faint depressions, color as blade.

*Veins (abaxial surface)*.—Appear as very faint depressions, color as blade, except midrib raised approximately 0.25 mm. with very lightly pubescence, color 175D, towards petiole.

Inflorescence::

*Flower type and habit*.—Globular to bowl shaped, held upright.

*Persistent or self-cleaning*.—Self cleaning.

*Quantity*.—One bud per node; more than 500 buds per plant in March.

*Natural flowering season*.—Commencing in late fall and peaking in early spring (mid-March to late March).

*Age of plants when first flowering*.—Most plants flower within the first year of growth from budding.

*Flower longevity on the plant*.—7-9 days from first opening to shedding of tepals.

*Fragrance*.—Honeyed perfume.

*Shape*.—Globular opening to bowl shaped with maturity.

*Diameter*.—30 mm.-35 mm.

*Depth (height)*.—25 mm.-30 mm. from tepal base.

*Flower buds (prior to showing color)*.—Shape: Ovoid. Dimensions: 22 mm.-24 mm. in length, 14 mm.-18 mm. in diameter. Color: Green 146D beneath (when scraped) dense dark brown pubescence. Hairs: very short, less than 0.25 mm in length, color ranges between 165A and 200D.

*Tepals*.—Number: 6. Arrangement: Overlapping. Strength: Weak: tepals fall away with light touch. Flowers will shatter in high wind. Dimensions: 35 mm. in length and 18 mm. in width. Shape: Broadly elliptic. Apex: Rounded. Base: Truncate. Margin: Entire. Surface texture: Waxy, glabrous. Color (both surfaces, excluding margin): Ground color, light cream-pink 155D with flecks or mottling ranging between 186D and 186A. Color (margin, both surfaces): Ranges between 64A and 64B.

*Peduncles*.—Dimensions: Approximately 15 mm. in length and 6 mm. in diameter. Color: As bud: green 146D beneath (when scraped) dense dark brown pubescence. Hairs very short, less than 0.25 mm. in length, color ranges between 165A and 200D.

Reproductive organs:

*Stamens*.—Quantity: 45-50.

*Filament dimensions*.—Length: 9 mm.-11 mm.; diameter 1 mm.

*Filament color.*—77A.
*Anther shape.*—Awl shaped, longitudinally furrowed terminating in small conical apical tip.
*Anther dimensions.*—5 mm.-6 mm. in length, 2 mm. in width.
*Anther color.*—163C, except apical tip 79A.
*Pollen amount.*—None observed.
*Pistil quantity.*—1.
*Pistil length.*—19 mm. including pistil stem (6 mm. in length) and terminal carpel cluster (13 mm. in length).
*Pistil diameter.*—2 mm. (pistil stem) and 4 mm (carpel cluster).
*Stigma shape.*—Round.
*Style length.*—Approximately 3 mm.
*Ovary.*—Observed immature and undeveloped. Shape approximately spherical, color 144C.

Seed: No seed has been observed.

COMPARISON WITH PARENTS

Whereas the flowers of the male parent, an unnamed *Magnolia laevifolia*, are pale purple in color, and the flowers of the female parent, an unnamed *Magnolia figo*, are cream-white in color, the flowers of 'HYB01' are purple-red in color and exhibit dark purple-red margins.

COMPARISON WITH CLOSEST KNOWN VARIETY

The closest comparison variety known to the inventor is the inventor's co-pending variety, *Magnolia* Plant Named 'SL01' which shares the same parentage. In comparison, mature plants of 'HYB01' are slightly taller and broader. The leaves of 'HYB01' are longer and wider than the leaves of 'SL01'. The flowers of 'HYB01' are red-purple in color with darker red-purple tepal margins, whereas the flowers of 'SL01' are predominantly cream in color.

I claim:

1. A new and distinct cultivar of *Magnolia* plant named 'HYB01' as described and illustrated herein.

* * * * *